(12) United States Patent
Pierre et al.

(10) Patent No.: US 9,198,796 B2
(45) Date of Patent: Dec. 1, 2015

(54) CONVECTIVE BLANKET WITH DISCONTINUOUS AIR FLOW GUIDES AND AIR FLOW PATTERNS

(75) Inventors: Joseph Pierre, Brockton, MA (US); Rachel Starr, Randolph, MA (US)

(73) Assignee: Smiths Medical ASD, Inc., Rockland, MA (US)

( * ) Notice: Subject to any disclaimer, the term of this patent is extended or adjusted under 35 U.S.C. 154(b) by 1501 days.

(21) Appl. No.: 11/798,973

(22) Filed: May 18, 2007

(65) Prior Publication Data

US 2008/0288034 A1  Nov. 20, 2008

(51) Int. Cl.
*A61F 7/00* (2006.01)
*A61F 7/12* (2006.01)
*A47C 27/00* (2006.01)

(52) U.S. Cl.
CPC ......... *A61F 7/0097* (2013.01); *A61F 2007/006* (2013.01)

(58) Field of Classification Search
USPC ......... 607/96, 104, 108–112, 113; 5/421, 423
See application file for complete search history.

(56) References Cited

U.S. PATENT DOCUMENTS

| 4,867,230 A * | 9/1989 | Voss ................................. 165/46 |
| 5,184,612 A | 2/1993 | Augustine |
| 5,300,102 A | 4/1994 | Augustine |
| 5,324,320 A | 6/1994 | Augustine |
| 5,336,250 A | 8/1994 | Augustine |
| 5,350,417 A * | 9/1994 | Augustine ..................... 607/104 |
| 5,620,482 A | 4/1997 | Augustine |
| 5,632,769 A | 5/1997 | Kappel et al. |
| 5,643,337 A | 7/1997 | Kappel et al. |
| 5,735,890 A | 4/1998 | Kappel et al. |
| 5,860,292 A * | 1/1999 | Augustine et al. ........... 62/259.3 |
| 5,941,907 A | 8/1999 | Augustine |
| 5,989,285 A | 11/1999 | DeVilbiss |
| 6,013,098 A | 1/2000 | Kappel et al. |
| 6,086,609 A * | 7/2000 | Buckley ........................ 607/104 |
| 6,102,936 A * | 8/2000 | Augustine et al. ............. 607/96 |
| 6,156,058 A | 12/2000 | Kappel et al. |
| 6,176,870 B1 | 1/2001 | Augustine |
| 6,203,567 B1 | 3/2001 | Augustine |
| 6,287,327 B1 | 9/2001 | Augustine |
| 6,544,283 B2 | 4/2003 | Augustine |
| 6,558,413 B2 | 5/2003 | Augustine |
| RE38,462 E | 3/2004 | Augustine |
| 2001/0041922 A1 * | 11/2001 | Augustine et al. ............ 607/107 |

* cited by examiner

*Primary Examiner* — Ryan Henderson
(74) *Attorney, Agent, or Firm* — Louis Woo

(57) ABSTRACT

A convective blanket has multiple sets of discontinuous bonding strips that bond or attach its upper layer to its lower layer to form a number of air flow guides within the blanket. There is at least one set of substantially parallel discontinuous strips proximate to the air input port of the blanket and another set of substantially parallel discontinuous strips remote from the air input port. For each set of in parallel discontinuous bond strips, the respective distal and proximal ends of each successive strips are aligned with the distal and proximal ends of a corresponding substantially in parallel strip to effect a cross channel so that air flowing along the air flow guide may escape to different sections of the blanket. To output the heated air from the blanket, respective single rows of successively spaced air holes are formed adjacent to and substantially along the length of the discontinuous bond strips that are located proximate to the air input port. For those sets of discontinuous bond strips that are remote from the air input port, there is provided adjacent to and substantially along the length of each of those strips multiple rows of successively spaced holes.

17 Claims, 3 Drawing Sheets

CONVECTIVE BLANKET WITH DISCONTINUOUS AIR FLOW GUIDES AND AIR FLOW PATTERNS

FIELD OF THE INVENTION

The present invention relates to inflatable convection blankets and more particularly to a blanket having a particular air flow configuration and air output patterns.

BACKGROUND OF THE INVENTION

To regulate the body temperature of a patient so as to prevent hypothermia to the patient in a medical environment, an inflatable convective blanket that provides a constant stream of warmed air is used. To provide uniform warmth to the patient, after heated air is input to the blanket for inflating the same, the flow pattern of the heated air, as well as the output of the warmed air from the blanket, needs to be regulated or guided in such a way as to eliminate, as much as possible, the difference in temperature of the warmed air output from the area of the blanket close to where the heated air is input to the blanket and the area of the blanket far away from where the heated air is input to the blanket.

One of the ways in which the prior art attempts to regulate the patterns of the flow of air in the blanket as well as to equalize the temperature of the heated air output from the various sections of a convection blanket is disclosed in U.S. Pat. No. 5,324,320, and its progeny U.S. Pat. Nos. 6,287,327 and 6,558,413. Those patents disclose a blanket that has a number of inflation cuffs, or tubes, longitudinally aligned along the length of the blanket. Passageways are provided between adjacent inflation cuffs, and staggered from cuff to cuff, so that each passageway would connect only adjacent cuffs and heated air can traverse between the cuffs. To equalize the temperature of the output air, in addition to having vent ports at the blanket, the apertures, or holes, wherethrough the heated air outputs from the blanket are designed into a pattern whereby the density of the apertures from the central portion of the blanket increase from the center portion of the blanket to the outer edges of the blanket. The configuration of the output air apertures of the above-discussed prior art blanket would work so long as the blanket is made up of a number of adjacent inflation cuffs, or tubes, longitudinally formed along the blanket. However, as convective blankets have now evolved into more than just inflatable self-erecting blankets which do not have the adjacent cuff configuration as the prior art blanket disclosed in the '320 patent, the flow pattern of the air in these non-self-erecting convective blankets need to be regulated so that the temperature gradient of the heated air output from such a blanket not vary substantially among the different sections of the blanket.

SUMMARY OF THE PRESENT INVENTION

The inflatable convection blanket of the instant invention is made of an upper air impermeable layer and a lower impermeable layer that are selectively bonded to each other substantially at their respective peripheries. A plurality of non-contiguous strips or seams whereby selective portions of the upper and lower layers away from the periphery are bonded to each other are formed at various sections of the blanket. Some of these strips are aligned, for example along the longitudinal axis of the blanket, to form a guide whereby air input to the blanket via an air input port flows. Two sets of such aligned strips that run parallel to each other form an air flow guide or a through channel in the blanket where the air input into the blanket is directed to flow in a given direction. Each set of the strips is made up of multiple non-contiguous strips, for example at least two. For each set of the multiple strips, the proximal and distal ends of each of the strips are in alignment with the proximal and distal ends, respectively, of a corresponding strip of another set of non-contiguous strips that make up the air flow guide channel. Accordingly, a cross channel is formed in the blanket structure for the air flow guide between the respective distal ends of the first of two successive non-contiguous strips and the respective proximal ends of the second of the two successive non-contiguous strips. Air being directed by the airflow guide can therefore escape from the airflow guide through such cross channel to other sections of the blanket.

To enable the heated air input to the blanket to exit from the blanket to thereby warm a patient placed on the blanket, the upper layer of the blanket, onto which the patient is placed, is manufactured to have a plurality of apertures, or holes, thereat for the heated air to escape. For the instant inventive blanket, the holes of the upper layer of the blanket are configured in the form of rows, with at least one row of equally spaced holes formed adjacent to each of the sets of the non-contiguous multiple strips that are located proximate to the air input port, where the heated air is input to the blanket. In order to equalize the temperature gradient for the warmed air output from the blanket, the air vent at the side, or far end, of the blanket remote or away from the air input port are configured in the form of at least two substantially parallel rows of successively spaced holes adjacent to each of the set of non-contiguous strips that form the air flow guide at that section of the blanket. With such configured holes and the air flow guides for the inventive blanket, it was found that a patient, for example an infant or child placed on the blanket, is bathed in an envelope of warm air which temperature gradient does not substantially vary across the surface of the upper layer.

A patient tends to lose a substantial amount of heat from his head. To remedy this shortcoming, the inventive blanket is further designed to have a warmed air output sealed section where the head of the patient tends to rest on, when the patient is placed on the blanket. To properly warm the head of the patient, the side of the sealed section closest to the air intake port is configured to have a row of successive holes that follows the curvature of that portion of the sealed section, whereas the side of the sealed section away from the air input port is configured to have at least two parallel rows of holes that follow the curvature of that portion of the sealed section, in order to equalize the warmth of the air bath at the sealed head section by varying the amount of warm air output at the head portion of the blanket.

The instant invention is therefore directed to an inflatable blanket that comprises an upper air impermeable layer with a lower air impermeable layer bonded thereto selectively along the periphery of the upper layer to form an inflatable structure, and a plurality of non-contiguous strips formed along the structure by the bonding of the upper and lower layers at selective areas of the structure. For the inventive blanket, there are at least two sets of multiple strips that run parallel to each other along the structure. Each set of the strips has at least two strips in longitudinal alignment with each other, with the two sets of parallel multiple strips forming a discontinuous air flow guide where the respective proximal and distal ends of each of the strips for the first of the two sets of strips being aligned with the respective proximal and distal ends of a corresponding strip for the second of the two sets of strips to form at least one cross channel along the air flow guide, so that some of the air flowing along the air flow guide may be directed to other sections of the structure by way of the cross channel.

Another aspect of inventive blanket is that an air input port is provided at the blanket where heated air under pressure is input to the blanket. Apertures or holes are formed in the upper layer of the blanket to output the input air, with respective rows of successively spaced holes being formed adjacent to the plurality of strips.

Yet another aspect of the present invention is that only one row of holes is provided adjacent to the multiple strips that form the air flow guide proximate to the air input port, and at least two substantially parallel rows of holes are provided adjacent a set of multiple strips that form the air flow guide at an area of the blanket that is far removed from the air input port.

A second embodiment of the instant inventive blanket includes an inflatable blanket that comprises a structure having an upper air impermeable layer bonded at selective sections of its periphery to a lower air impermeable layer, at least one air input port provided at the structure to enable air under pressure to be input to the structure, at least a first set of holes formed at the upper layer along one side of the structure proximate to the air input port to enable heated air input to the structure to exit, and at least a second set of holes separated by a given distance from the first set of holes formed on the upper layer along another side of the structure away from the air input port to enable heated air input to the structure to exit. The number of holes for the second set of holes is greater than the number of holes for the first set, with the number of holes for the second set being determined to be a number sufficiently greater than the number of holes for the first set to ensure that more heated air is output from the second set of holes than from the first set, so that a patient laying on the upper layer of the blanket would feel substantially the same level of warmth from the heated air output respectively from the first and second set of holes.

BRIEF DESCRIPTION OF THE FIGURES

The present invention will become apparent and the invention itself will be best understood with reference to the following description of the invention taken in conjunction with the accompanying drawings, wherein.

DETAILED DESCRIPTION OF THE INVENTION

Figure 1:
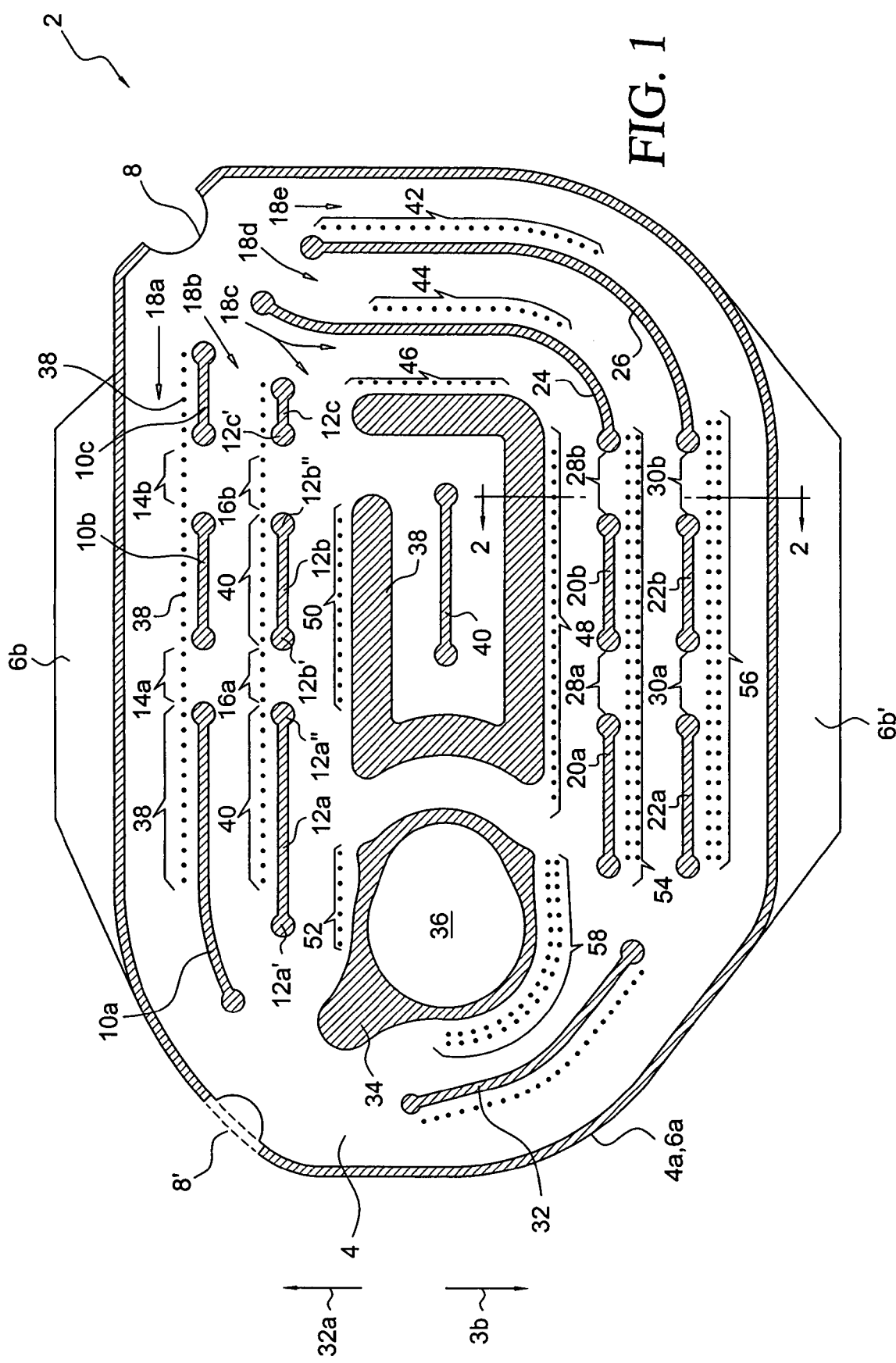
FIG. 1 is a plan view of the convective blanket of the instant invention.
Figure 2:
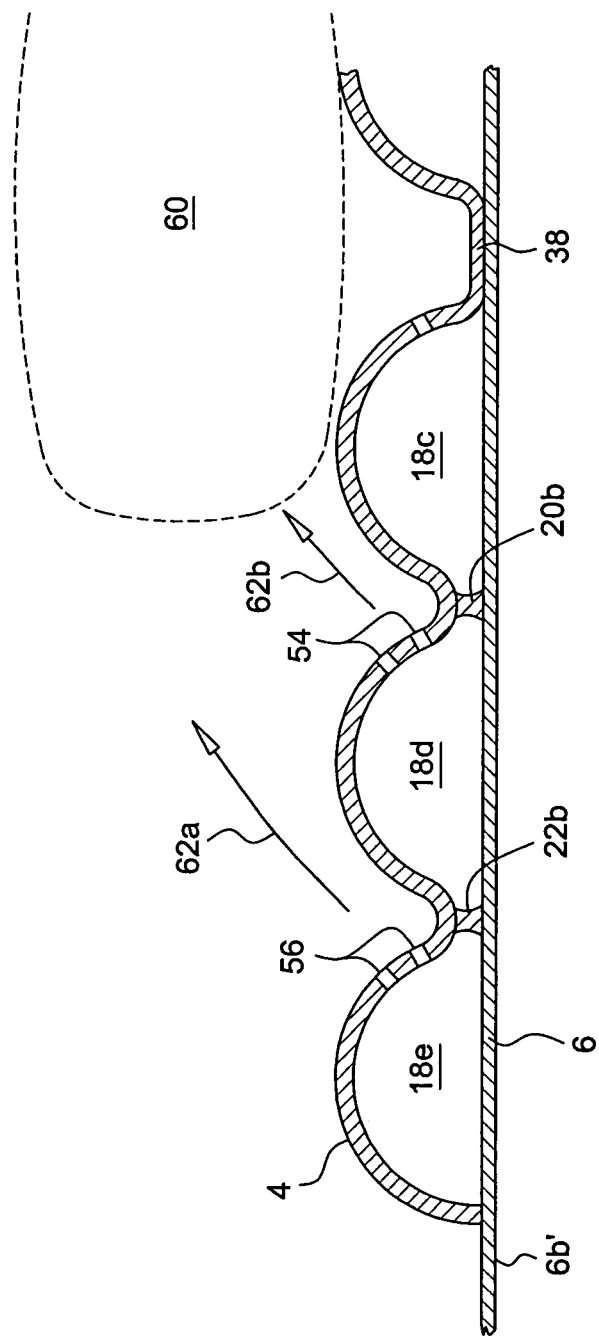
FIG. 2 is an enlarged cross-sectional view taken along line 2-2 of FIG. 1.

With reference to FIGS. 1 and 2, an exemplar convective blanket 2 of the instant invention is shown to have a first sheet or an upper layer 4 and a second sheet or lower layer 6. The upper layer 4 and the lower layer 6 are selectively bonded or attached, by means of adhesive or other means for example, at their respective peripheries 4a and 6a so that an inflatable structure is formed. The upper and lower layers 4, 6 are made from an air impermeable material, for example from woven materials conventionally known for the manufacture of the layers of convective blankets. Being air impermeable, fluid such as for example air could not escape from the blanket structure other than from apertures or holes formed on either the upper layer 4 or the lower layer 6.

As shown, there are two side extensions 6b, 6b' for the lower layer 6 that extend beyond the side peripheries of upper layer 4. The extensions 6b, 6b' are there for securing the blanket 4 to a bed or table, if necessary, as conventionally done. Although shown as extensions of lower layer 6, extensions 6b and 6b' may in actuality be a separate layer or sheet that is bonded to lower layer 6. such additional sheet or layer is not shown in the figures for the sake of simplicity in the discussion of the inventive blanket.

In order to input air to inflate blanket 2, at least one air input port 8 is formed at blanket 2, for example at a junction of peripheries 4a and 6a of the upper layer 4 and the lower layer 6, respectively, as shown in FIG. 1. An optional air input port 8' is also provided at the blanket and is used only in those circumstances where it is desirable that the heated air be input to the blanket close to the head of the patient. Heated air is input to blanket 2 for inflating the same by means of a conventional convective warmer, such as for example those sold by the assignee of the instant application. For conventional use, optional air input port 8' is closed and air input port 8 is the primary source for inputting air to blanket 2.

To control the flow of air in blanket 2, the upper layer 4 and the lower layer 6 are bonded or attached together at a number of places in the form of either longitudinal strips or contoured strips that define a particular area of the blanket. The longitudinal strips are represented for example by strips 10a-10c and their corresponding substantially in parallel strips 12a-12c. These longitudinal strips comprise a number of non-contiguous strips in that strip 10a does not extend to strip 10b, and strip 10b does not extend to strip 10c. Alternatively, strips 10a-10c together may be considered as parts of a discontinuous air flow guide. The same is true with respect to strips 12a, 12b and 12c. These discontinuous or non-contiguous strips are formed on blanket 2 in such a way that the respective distal and proximal ends of successive strips would form respective through passages, as designated for example by spaces 14a and 14b for strips 10a and 10b, respectively, that are substantially transverse to the longitudinal axis of the discontinuous air flow guides in blanket 2.

For discontinuous strips 12a, 12b and 12c that lie substantially in parallel to strips 10a, 10b and 10c, the distal end of strip 12a, designated 12a", is separated from the proximal end 12b' of strip 12b by a space 16a while the distal end 12b" of strip 12b is separated from the proximal end 12c' of strip 12c by a space 16b. These spaces 16 also form through passages between successive pairs of the discontinuous strips 12a-12c.

For the instant invention blanket, the substantially in parallel discontinuous strips 10 and 12 are formed on the blanket such that spaces 14a and 16a, and spaces 14b and 16b are in respective alignments so that respective cross channels are formed from the aligned spaces 14a, 16a and 14b, 16b of the parallel discontinuous strips 10 and 12.

Being substantially parallel, the two sets of discontinuous strips 10 and 12 form an air flow channel or guide to route air input from air input port 8 therealong. Additional air channels or air flow guides are formed by discontinuous strips 10 and 12 in blanket 2, i.e., the air channel between strips 10 and peripheries 4a/6a, and the air channel between strips 12 and the contoured strips 34 and 38. The air flows through these air channels established by the air flow guiding strips are represented by directional arrows 18a-18e. For the instant invention, the in parallel sets of discontinuous strips may therefore be considered to effect air flow guides.

Given that there are cross channels, as represented by the pairs of openings 14a, 16a and 14b, 16b, along the air flow guide created by the set of discontinuous strips 14 and 16, portions of the air flowing through the air guide channels, as represented by air flow arrows 18a-18c, are routed to other sections of the blanket.

A second pair of substantially parallel sets of discontinuous strips is represented by strips 20a, 20b and strips 22a and 22b. Strips 20a and 20b may be considered as portions of discontinuous strip 24 while strips 22a and 22b may be considered as portions of discontinuous strip 26. Strips 20a and 20b are separated by a through passage space 28a while strip 20b and strip 24 are separated by a through passage space 28b. Likewise, strip 22a is separated from strip 22b by a through passage space 30a while strip 22b is separated from strip 26 by a through passage space 30b. An additional contoured longitudinal strip 32 whereby the upper layer is bonded to the lower layer 6 is also provided on blanket 2.

A further set of strips, shown in FIG. 1 to be wider than the longitudinal strips discussed above, is provided in blanket 2 by the bonding of upper layer 4 to lower layer 6. The first such wider bonding strip is represented by bonded section 34 that seals area 36 of the blanket. A second wider section where upper layer 4 is bonded to lower layer 6 is represented by bonded section 38. A small longitudinal bonding strip 40 bonds upper layer 4 to lower layer 6 in the middle of the area bounded by wider strip 38. Although shown as wider strips, sections 36 and 38 may in actuality be defined by bond strips that have the same width as the earlier discussed strips. In other words, all bond strips for the exemplar blanket 2 shown in FIG. 1 may have the same width.

A cross section of blanket 2 where air passes is illustrated in FIG. 2. As shown, air is being guided by the air flow guides established by the in parallel discontinuous strips 20a, 20b, 24 and 22a, 22b and 26. As shown by the cross sectional illustration of FIG. 2, air may flow through cross channels 30b and 28b to intermix with the air flowing through the other channels that are represented by the air flows 18e, 18d and 18c.

The heated air input to blanket 2 tends to cool down as it travels along the blanket. Accordingly, the areas of the blanket far removed or remote from the air input port, such as for example those areas of the blanket bounded by strips 20a, 20b, and 22a and 22b, tend to be inflated by air that has a lower temperature than the warmed air traversing in the area of the blanket bounded by strips 10a, 10b, 10c and 12a, 12b and 12c. Prior to the instant invention, to remedy this shortcoming, one type of convective blanket, as described in the aforenoted '320 patent, has an increasing number of holes for each of the longitudinal tubes that is further away from the center tube and closer towards both edges of the blanket. The number of holes for each longitudinal tube of the blanket therefore increases towards both side edges of the blanket, as represented for example by directional arrows 32a and 32b of FIG. 1. For this type of blanket, the air output is incrementally increased from the center of the blanket towards the edges of the blanket. The blanket disclosed in the '320 patent is made up of adjacent tubes and is meant to be used to cover a patient.

The instant inventive blanket, on the other hand, is a blanket onto which a patient is placed. Therefore, the air flow pattern for the instant blanket is substantially different from the prior art blanket, which does not have air flow guides made up of discontinuous strips with corresponding cross over channels effected by matching proximal and distal ends for directing air to different areas within the blanket.

To effect a blanket that outputs air with substantially the same degree of warmth at a portion of the blanket remote from the air input port as compared to a portion proximate to the air input port, the inventors found that only certain areas of the upper layer 4 along the bonded strips needed to have holes to allow the heated air to output or exit from the blanket. Thus, for the sets of discontinuous strips proximate to the air input port 8, such as for example strips 10a-10c and strips 12a-12c, there are formed on upper layer 4 a single row or set of successively spaced holes 39 adjacent substantially along the length of the set of discontinuous strips 10a-10c, and a second row or set of successively spaced holes 40 adjacent substantially along the length of the set of discontinuous strips 12a-12c, per shown in FIG. 1. Respective single rows or sets of holes 42, 44 and 46 are also provided substantially lengthwise along strips 24, 26, and the cross section of wider strip 38, respectively. All of those strips may be considered to be located proximate to air input port 8. Air substantially of a given temperature is output from the rows of holes 39, 40, 42, 44 and 46. Additional rows or sets of successively spaced holes 48 and 50 along the longitudinal sections of wider bond strip 38 are also provided. A single row or set of holes 52 is provided adjacent to the longitudinal portion of bonded strip 34.

To ensure that a patient placed on top of blanket 2 is evenly warmed thereby, a set of holes that is made up of at least two rows or family of holes (shown as parallel in FIG. 1) is formed adjacent to and substantially along the length of each set of the discontinuous bond strips remote from the air input port. For example, a set of two rows of successively spaced holes 54 is placed adjacent the set of discontinuous strips 20a and 20b, while another set of double rows of successively spaced holes 56 is placed adjacent the set of discontinuous bond strips 22a and 22b. There is moreover another set of two rows of successively spaced holes 58 placed adjacent a portion of the bonding strip 34 at one side of sealed section 36. By providing sets of multiple rows of holes adjacent to sets of discontinuous bond strips that are remote from the air input port, the amount of air output therefrom, for example from hole sets 54 and 56, is greater than the amount of air output from the sets of single hole rows, for example from rows 38, 40, 42, 44 and 46, so that the patient feels substantially the same amount of warmth at those disparate sections of the blanket. In other words, the patient is substantially enveloped by the same warm bath of heated air from substantially all areas of the blanket.

As the head of the patient tends to lose the most heat, by providing two substantially in parallel rows of successively spaced holes such as 58 adjacent to sealed section 36 where the head of the patient presumably is placed, the amount of heat loss from the head of the patient is reduced. Although two rows of holes are shown for each of sets 54, 56 and 58, it should be appreciated that more than two rows of holes may be formed adjacent to those discontinuous sets of bond strips when necessary to balance the amount of heated air output at those portions of the blanket that are remote from the air input port 8. The number of holes to be formed at those sections adjacent to the sets of discontinuous bond strips remote from the air input port needs to be a number that is sufficiently greater than the number of holes for the single rows of holes that are formed adjacent to the sets of discontinuous bond strips proximate to the air input port, so that the amount of heat provided to the patient at the various sections of the blanket does not vary substantially.

Figure 3:
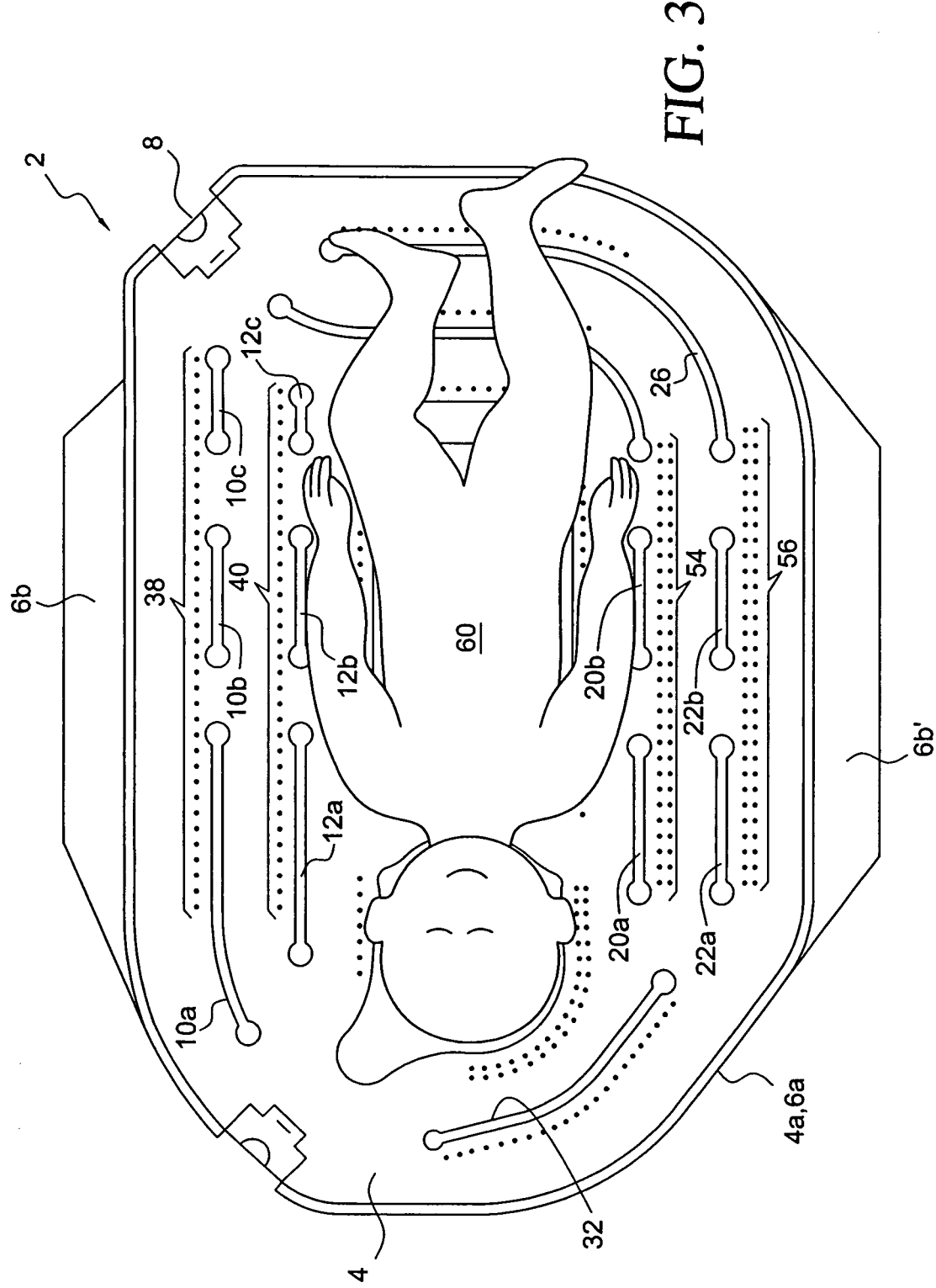
FIG. 3 is another view of the inventive blanket onto which a patient is placed.

FIG. 3 shows a patient, in this instance an infant 60, placed on top of blanket 2, with his head resting on section 36 and his main body resting on the area of the blanket defined by bond strip 38 (FIG. 1), so that different amounts of air are directed to him from the plurality of rows of holes that are formed adjacent the different sets of discontinuous bond strips. As best shown in FIG. 2, when the blanket is inflated and air flows along the various air flow guides, upper layer 4 is inflated so that the double rows of holes, for example 54 and 56, would tend to point toward patient 60, shown in dotted box in FIG. 2, so that the warmed air is output directly toward the patient to establish a bath of warm air that envelops the patient. The directions of exemplar flows of the warm air towards the patient are indicated by directional arrows 62*a* and 62*b*.

The invention claimed is:

1. A blanket, comprising:
   an upper sheet and a lower sheet each having a periphery, the upper sheet and the lower sheet bonded together at their respective peripheries to form an inflatable structure consisting of the upper and lower sheets, the upper and lower sheets each being air impermeable;
   at least one air flow channel extending longitudinally along the structure away from a head portion of the structure, the air flow channel being defined by two sets of substantially in parallel non-contiguous strips that selectively bond the upper and lower sheets to each other at least a given distance longitudinally along the structure to form a non-inflatable section of the blanket, there being no other bonding of the upper and lower sheets between the two sets of substantially in parallel non-contiguous strips so that air flows uninterrupted through and is guided by the air flow channel along at least the given distance;
   wherein each set of the non-contiguous strips has at least two longitudinal strips of non-inflatable sections of the blanket in longitudinal alignment with each other, each of the longitudinal strips has a proximal end and a distal end, the respective proximal and distal ends of each of the strips of one of the two sets of non-contiguous strips being aligned with the respective proximal and distal ends of a corresponding strip for other of the two sets of non-contiguous strips to from at least one cross channel along the air flow channel to enable some of the air flowing through the air flow channel to escape to other sections of the structure; and
   a substantially rectangular area at a body portion of the structure formed by a substantially rectangular strip that bonds the upper sheet and the lower sheet together, the respective ends of the substantially rectangular strip being separated from each other so that the substantially rectangular area is not completely sealed off from the rest of the structure.

2. Blanket of claim 1, further comprising:
   a non-ending strip at the head portion of the structure bonding the upper and lower sheets to form a sealed area whereon a head of a subject rests when the subject is placed onto the structure.

3. Blanket of claim 1, further comprising:
   at least one port to enable air to be input into the structure for inflating the structure; and
   respective rows of holes formed on the upper sheet adjacent the strips for outputting the input air.

4. Blanket of claim 1, wherein the structure comprises two air flow channels, wherein one air flow channel extends along one longitudinal side of the structure and other air flow channel extends along other longitudinal side of the structure, each of the air flow channels defined by two sets of substantially in parallel non-contiguous strips that selectively bond the upper and lower sheets together, there being no other bonding of the upper and lower sheets between the respective sets of substantially in parallel non-continuous strips.

5. Blanket of claim 1, further comprising:
   at least a first set of holes formed on the upper sheet along one side of the structure positioned relative to a port where air is input to the structure for inflating the structure; and
   at least a second set of holes formed on the upper sheet along another side of the structure far removed from the input port;
   wherein the first set being one row of successive holes and wherein the second set being at least two rows of successive holes.

6. Blanket of claim 1, wherein the at least one air flow channel further comprises two substantially in parallel contoured strips each being one portion of one of the two sets of non-continuous strips, each of the contoured strips has a proximal end spaced from the distal end of a longitudinal strip of a corresponding set of non-continuous strips, the respective distal ends of the contoured strips positioned proximately to a port of the structure to guide the air input to the port through the at least one air flow channel.

7. Blanket of claim 2, further comprising:
   one set of holes formed on the upper sheet at an area adjacent to the sealed area for outputting air directed to the head of the subject;
   another set of holes formed on the upper sheet at another area adjacent to the sealed area for outputting air to the head of the subject from a different direction;
   wherein the one or the other set of holes that is located further away from a port whereinto a heated air is input into the structure has a greater number of holes than the one or other set of holes located closer to the port so that the heated air output from the set of holes further away from the port has substantially the same warmth as the heated air output from the set of holes closer to the port.

8. A blanket, comprising:
   an inflatable structure consisting of an upper air impermeable sheet and a lower air impermeable sheet bonded together at their respective peripheries;
   at least one port provided at the structure to enable air to be input to the structure;
   at least two sets of substantially in parallel non-continuous strips each having a proximal end and a distal end extending longitudinally a given distance along the structure, each set of non-continuous strips having at least two longitudinal strips in longitudinal alignment with each other, the longitudinal strips bonding the upper and lower sheets together to form non-inflatable sections of the blanket, the two sets of substantially in parallel non-continuous strips forming one air flow channel to guide air flow therethrough, there being no other bonding of the upper and lower sheets between the two sets of non-continuous strips so that there is no interruption to the air flowing along the air flow channel, the respective proximal and distal ends of each of the strips of one of the two sets of non-contiguous strips being aligned with the respective proximal and distal ends of a corresponding strip for other of the two sets of non-contiguous strips to from at least one cross channel along the air flow channel to enable some of the air flowing through the air flow channel to escape to other sections of the structure; and
   a plurality of holes at the upper sheet adjacent to the strips to allow air input to the structure to exit upwardly from the upper sheet; and
   a substantially rectangular area formed by a substantially rectangular strip that bonds the upper sheet and the lower sheet together, the respective ends of the substantially rectangular strip being separated from each other.

9. Blanket of claim 8, further comprising:
a non-ending strip bonding the upper and lower sheets at a head portion of the structure to form a sealed area whereon a head of a subject rests when the subject is placed onto the structure.

10. Blanket of claim 9, further comprising:
one row of holes formed on the upper sheet adjacent an area of the sealed area for outputting air directed to the head of the subject, and at least two rows of holes formed on the upper sheet adjacent another area of the sealed area further away from the input port than the one row of holes for outputting air to the head of the subject from a different direction.

11. Blanket of claim 8, wherein the plurality of holes comprise one row of successive holes provided at the upper sheet adjacent substantially lengthwise to each of the strips of the two sets of substantially in parallel non-continuous strips.

12. Blanket of claim 8, wherein the structure comprises two air flow channels, wherein one air flow channel extends along one longitudinal side of the structure and other air flow channel extends along other longitudinal side of the structure, each of the air flow channels defined by two sets of substantially in parallel non-contiguous strips that selectively bond the upper and lower sheets together, there being no other bonding of the upper and lower sheets between the respective sets of substantially in parallel non-continuous strips.

13. Blanket of claim 8, wherein the at least one air flow channel further comprises two substantially in parallel contoured strips each being one portion of one of the two sets of non-continuous strips, each of the contoured strips has a proximal end spaced from the distal end of a longitudinal strip of a corresponding set of non-continuous strips, the respective distal ends of the contoured strips positioned proximately to the port to guide the air input to the port through the air flow channel.

14. A blanket, comprising:
an upper sheet and a lower sheet each having a periphery, the upper sheet and the lower sheet bonded together at their respective peripheries to form an inflatable structure consisting of the upper and lower sheets, the upper and lower sheets each being air impermeable;
a non-ending strip at a head portion of the structure bonding the upper and lower sheets to form a sealed area whereon a head of a subject rests when the subject is placed onto the structure;
at least one air flow channel extending longitudinally along the structure in a body portion of the structure, the air flow channel being defined by two sets of substantially in parallel non-contiguous strips that selectively bond the upper and lower sheets to each other to form non-inflatable sections of the blanket at least a given distance longitudinally along the body portion, there being no other bonding of the upper and lower sheets between the two sets of substantially in parallel non-contiguous strips so that air flows uninterrupted through and is guided by the air flow channel along at least the given distance;
wherein each set of the non-contiguous strips has at least two longitudinal strips in longitudinal alignment with each other, each of the longitudinal strips has a proximal end and a distal end, the respective proximal and distal ends of each of the strips of one of the two sets of non-contiguous strips being aligned with the respective proximal and distal ends of a corresponding strip for other of the two sets of non-contiguous strips to from at least one cross channel along the air flow channel to enable some of the air flowing through the air flow channel to escape to other sections of the structure; and
a substantially rectangular area at a body portion of the structure formed by a substantially rectangular strip that bonds the upper sheet and the lower sheet together, the respective ends of the substantially rectangular strip being separated from each other.

15. Blanket of claim 14, wherein the structure comprises two air flow channels, wherein one air flow channel extends along one longitudinal side of the structure and other air flow channel extends along other longitudinal side of the structure, each of the air flow channels defined by two sets of substantially in parallel non-contiguous strips that selectively bond the upper and lower sheets together, there being no other bonding of the upper and lower sheets between the respective sets of substantially in parallel non-continuous strips.

16. Blanket of claim 14, further comprising at least one row of successively spaced holes at the upper sheet adjacent each of the strips.

17. Blanket of claim 14, wherein the at least one air flow channel further comprises two substantially in parallel contoured strips each being one portion of one of the two sets of non-continuous strips, each of the contoured strips has a proximal end spaced from the distal end of a longitudinal strip of a corresponding set of non-continuous strips, the respective distal ends of the contoured strips positioned proximately to the port to guide the air input to the port through the air flow channel.

\* \* \* \* \*